United States Patent
Laughlin et al.

(10) Patent No.: US 10,107,767 B1
(45) Date of Patent: Oct. 23, 2018

(54) AIRCRAFT INSPECTION SYSTEM WITH VISUALIZATION AND RECORDING

(71) Applicant: The Boeing Company, Chicago, IL (US)

(72) Inventors: Brian D. Laughlin, Wichita, KS (US); Richard T. Moore, Riverside, CA (US); Steven Curtis Franzman, Cerritos, CA (US); David R. Aguilar, Whittier, CA (US); Elizabeth Juhnke, Lynnwood, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/622,756

(22) Filed: Jun. 14, 2017

(51) Int. Cl.
| | |
|---|---|
| *G09G 5/00* | (2006.01) |
| *G01N 23/18* | (2018.01) |
| *G01M 5/00* | (2006.01) |
| *G01N 29/22* | (2006.01) |
| *G01N 29/44* | (2006.01) |

(Continued)

(52) U.S. Cl.
CPC .......... *G01N 23/18* (2013.01); *G01M 5/0033* (2013.01); *G01M 5/0075* (2013.01); *G01N 23/04* (2013.01); *G01N 29/225* (2013.01); *G01N 29/4409* (2013.01); *G01B 15/00* (2013.01); *G01N 29/22* (2013.01)

(58) Field of Classification Search
None
See application file for complete search history.

(56) References Cited

U.S. PATENT DOCUMENTS

| | | |
|---|---|---|
| 9,612,725 B1 | 4/2017 | Senesac |
| 2009/0289955 A1* | 11/2009 | Douris ................... G01C 21/20 345/630 |

(Continued)

FOREIGN PATENT DOCUMENTS

| | | |
|---|---|---|
| EP | 2787481 A1 | 10/2014 |
| WO | 2015102527 A1 | 7/2015 |

OTHER PUBLICATIONS

Greenfield, "Augmented Reality for Industry," Automation World, PMMI Media Group, copyright 2017, 4 pages, accessed Jun. 7, 2017. https://www.automationworld.com/article/industry-type/all/augmented-reality-industry.

(Continued)

*Primary Examiner* — Frank Chen
(74) *Attorney, Agent, or Firm* — Yee & Associates, P.C.

(57) ABSTRACT

A method, system, and apparatus for a vehicle inspection system comprising a mobile inspection device, a display system, a graphical user interface configured to be displayed on the display system, and a controller. The controller is configured to identify a position of the mobile inspection device within a vehicle and receives a user input comprising a group of gestures made by a human operator with respect to an item in a group of items in a field of view of the mobile inspection device based on the position of the mobile inspection device. The controller creates a note at a location with respect to the vehicle in association with the item in the field of view of the mobile inspection device in which the note is assigned to the location with respect to the vehicle and displays the note on the graphical user interface for the mobile inspection device.

27 Claims, 13 Drawing Sheets

(51) Int. Cl.
*G01N 23/04* (2018.01)
*G01B 15/00* (2006.01)

(56) References Cited

U.S. PATENT DOCUMENTS

| | | | |
|---|---|---|---|
| 2009/0319902 A1* | 12/2009 | Kneller | G06F 3/013 |
| | | | 715/733 |
| 2011/0066682 A1 | 3/2011 | Aldunate et al. | |
| 2012/0212414 A1 | 8/2012 | Osterhout et al. | |
| 2013/0070056 A1 | 3/2013 | Tripathi | |
| 2013/0169681 A1 | 7/2013 | Rasane et al. | |
| 2013/0222369 A1 | 8/2013 | Huston et al. | |
| 2014/0240349 A1* | 8/2014 | Tuukkanen | G06F 17/30244 |
| | | | 345/633 |
| 2017/0087465 A1 | 3/2017 | Lyons et al. | |
| 2017/0358142 A1* | 12/2017 | Lee | H04L 67/18 |

OTHER PUBLICATIONS

AREA, Augmented Reality for Enterprise Alliance, "Article Inspection," 3 pages, accessed Jun. 7, 2017. http://thearea.org/ar-assisted-article-inspection/.

"DAQRI Smart Glasses Scenario #1: Aviation Inspection," 4 pages, accessed Jun. 7, 2017. https://medium.com/©DAQRI/daqri-smart-glasses-scenario-1-aviation-inspection-5d42eb01628c#.zh7y8efnw.

EquipmentWord, "Caterpillar Augmented Reality Inspection Demo," YouTube.com, published Oct. 22, 2015, 3 pages. https://www.youtube.com/watch?v=S8jMgBimuxg.

Perla et al., "InspectAR: An Augmented Reality Inspection Framework for Industry," IEEE International Symposium on Mixed and Augmented Reality (ISMAR-Adjunct), Sep. 2016, pp. 355-356. (Abstract).

European Search Report, dated Jul. 16, 2018, regarding Application No. 18170605.2, 4 pages.

* cited by examiner

AIRCRAFT INSPECTION SYSTEM WITH VISUALIZATION AND RECORDING

BACKGROUND INFORMATION

1. Field

The present disclosure relates generally to aircraft, and in particular, to a method and system for inspecting aircraft with visualization and recording.

2. Background

In manufacturing aircraft for customers, many inspections are performed during the manufacturing process. The final inspection is performed by human operators. The final inspection is the last step performed prior to delivery of the aircraft to a customer. This final inspection currently employs physically marking and making notes during the inspection of the aircraft.

The physical marking may include applying tape or other markers to locations to identify areas in need of repair before delivery of the aircraft to the customer. Additionally, notes may be written on sheets of paper with adhesive backings that may be affixed to locations in the aircraft to provide described inconsistencies or repairs that may be needed.

Currently, these markers and physical notes are logged in a three-ring binder or notebook. The location and an identifier for the physical note may be logged in the three-ring binder.

The current inspection process is time consuming and inefficient. For example, the tape may fall off an item that is marked for rework. Notes may be misinterpreted. Also, penalties and fines may be imposed for tape and notes being left behind from locations in the aircraft. For example, tape may be missed in overhead storage bins in the aircraft.

Therefore, it would be desirable to have a method and apparatus that takes into account at least some of the issues discussed above, as well as other possible issues. For example, it would be desirable to have a method and apparatus that overcomes a technical problem with efficiently performing inspections in an aircraft.

SUMMARY

An embodiment of the present disclosure provides a vehicle inspection system. The vehicle inspection system comprises a mobile inspection device, a display system for the mobile inspection device, a graphical user interface, and a controller. The graphical user interface is configured to be displayed on the display system. The controller is configured to operate with the mobile inspection device. The controller is configured to identify a position of the mobile inspection device within a vehicle. The controller receives a user input comprising a group of gestures made by a human operator with respect to an item in a group of items in a field of view of the mobile inspection device based on the position of the mobile inspection device. The controller creates a note at a location with respect to the vehicle in association with the item in the field of view of the mobile inspection device in which the note is assigned to the location with respect to the vehicle. The controller displays the note in association with the item in the field of view on the graphical user interface on the display system for the mobile inspection device.

Another embodiment of the present disclosure provides an aircraft inspection system. The aircraft inspection system comprises a mobile inspection device, a user interface for the mobile inspection device, and a controller. The controller is configured to operate with the mobile inspection device. The controller is configured to identify a position of the mobile inspection device within an aircraft. The controller receives a user input comprising a group of gestures made by a human operator with respect an item in a field of view of the mobile inspection device based on the position of the mobile inspection device within the aircraft. The controller creates a note in association with the item in the group of items in the field of view of the mobile inspection device. The controller displays the note in association with the item in the field of view on a display system for the mobile inspection device, enabling immersion in an augmented reality environment.

Yet another embodiment of the present disclosure provides a method for inspecting a vehicle. The method comprises identifying a position of a mobile inspection device within the vehicle. The method receives a user input comprising a group of gestures made by a human operator with respect an item in a group of items in a field of view of the mobile inspection device based on the position of the mobile inspection device. The method creates a note at a location with respect to the vehicle in association with the item in the group of items in the field of view of the mobile inspection device in which the note is assigned to the location. The method displays the note in association with the item in the field of view on a graphical user interface on a display system for the mobile inspection device.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that currently used techniques to inspect vehicles, such as aircraft, take more time and effort than desired using physical and paper notes. The illustrative embodiments also recognize and take into account that currently used techniques for inspecting aircraft employ a disjointed collection of processing systems without real-time metrics and measures for gathering information about inconsistencies.

Thus, the illustrative embodiments provide a method and apparatus for inspecting vehicles. In one illustrative example, the process provides an augmented reality experience for the human operator performing the inspection. The process identifies a position of a mobile inspection device within the vehicle. A user input is received in which the user input comprises a group of gestures made by a human operator with respect an item in a group of items in a field of view of the mobile inspection device based on the position of the mobile inspection device. A note is created at a location with respect to the vehicle in association with the item in the group of items in the field of view of the mobile inspection device in which the note is assigned to the location. The note is displayed in association with the item in the field of view on the graphical user interface on a display system for the mobile inspection device.

Figure 1:
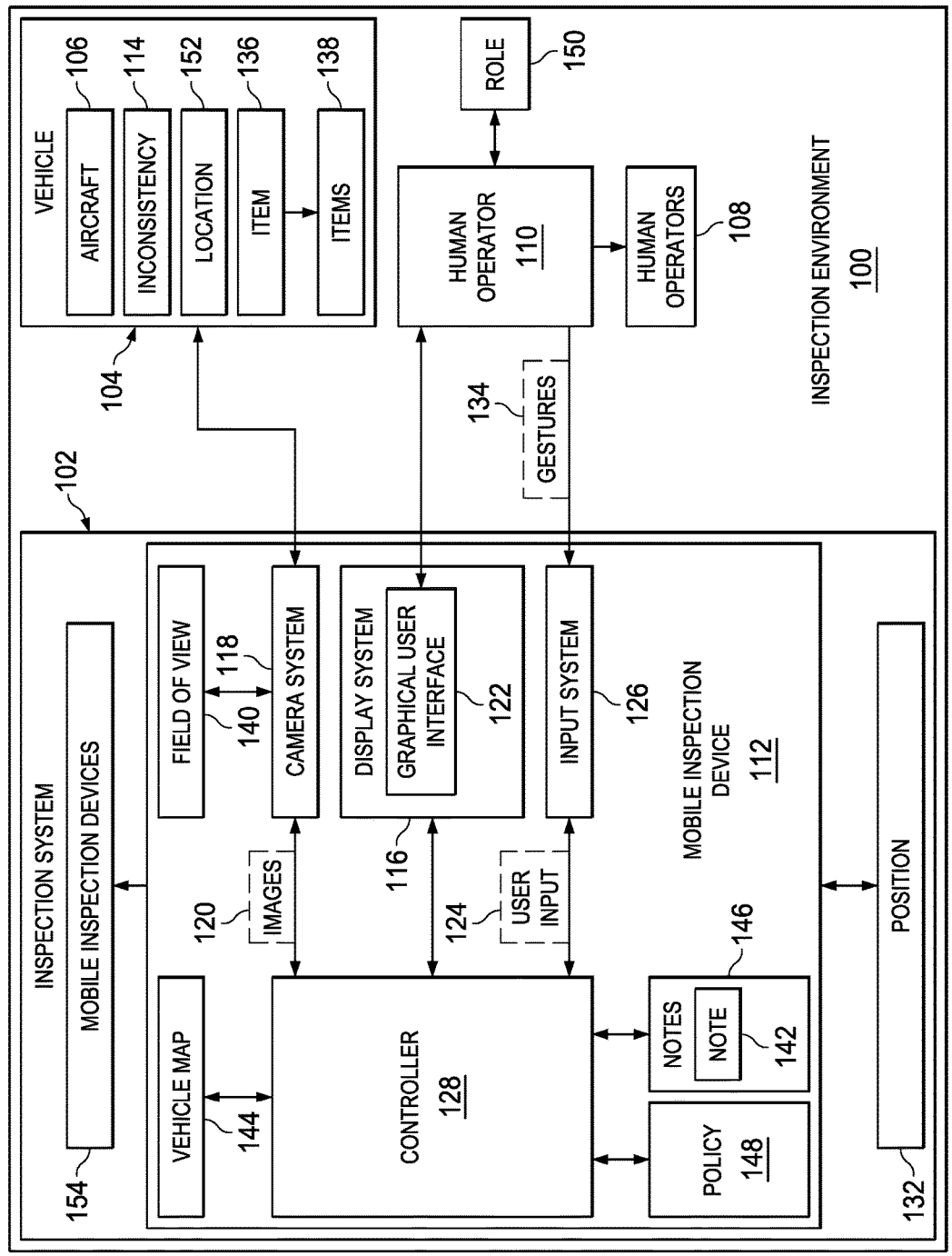
FIG. 1 is an illustration of a block diagram of an inspection environment in accordance with an illustrative embodiment.

With reference now to the figures, and in particular, with reference to FIG. 1, an illustration of a block diagram of an inspection environment is depicted in accordance with an illustrative embodiment. Inspection environment 100 includes inspection system 102. As depicted, inspection system 102 is utilized to inspect vehicle 104. In this illustrative example, vehicle 104 takes the form of aircraft 106. Aircraft 106 may be selected from one of a commercial airplane, a military jet, a rotorcraft, a helicopter, or some other suitable type of aircraft.

In this illustrative example, inspection system 102 is operated by one or more of human operators 108 to perform the inspection of vehicle 104. For example, human operator 110 in human operators 108 inspects vehicle 104 using mobile inspection device 112 in a group of mobile inspection devices 154 in inspection system 102.

As used herein, a "group of" when used with reference to items, means one or more items. For example, a group of mobile inspection devices 154 is one or more of mobile inspection devices 154.

As depicted, mobile inspection device 112 and other mobile inspection devices in the group of mobile inspection devices 154 are physical devices that may be carried and used by human operators 108. The group of mobile inspection devices 154 may be selected from at least one of a mobile phone, a head mounted display, mixed reality smart glasses, a tablet computer, or some other suitable type of device.

Human operator 110 may move relative to vehicle 104 to determine whether inconsistency 114 is present. The movement relative to vehicle 104 may be at least one of moving within vehicle 104 or around vehicle 104.

In this illustrative example, inconsistency 114 may take different forms. For example, inconsistency 114 is selected from least one of a scratch, a stain, a smudge, a missing part, a defective part, an incorrect part, or some other undesirable condition.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A, one of item B, and ten of item C; four of item B and seven of item C; or other suitable combinations.

As depicted, display system 116 and camera system 118 are present in mobile inspection device 112. These two systems may be integrated as part of mobile inspection device 112 or may be connected to or otherwise in communication with mobile inspection device 112. Display system 116 is a hardware system and comprises one or more display devices. Camera system 118 is a hardware system and also comprises one or more cameras that may be used to generate images 120 for display on display system 116.

Images 120 may be individual pictures or part of a video. In this illustrative example, images 120 may be displayed on display system 116 through graphical user interface 122 in mobile inspection device 112.

As depicted, human operator 108 is a person that may interact with graphical user interface 122 through user input 124 generated by input system 126 for mobile inspection device 112. Input system 126 is a physical hardware system and may be selected from at least one of a gesture recognition system, wired gloves, a stereo camera, a gesture based controller, a mouse, a track ball, a keyboard, a track pad or a touch screen tablet, a motion sensing input device, a cyber glove, a camera, a microphone, or some other suitable type of input device.

In this illustrative example, controller 128 is located in mobile inspection device 112 in inspection system 102. In another illustrative example, controller 128 may be located in a remote computer. As depicted, controller 128 is configured to perform operations when human operator 110 inspects vehicle 104. For example, during operation of controller 128, controller 128 operates with mobile inspection device 112 to identify position 132 of mobile inspection device 112 within vehicle 104. Mobile inspection device 112 may include devices such as a global positioning system (GPS) receiver, an accelerometer, an inertial navigation system, or some other suitable device for identifying position 132 of mobile inspection device 112.

In this illustrative example, position 132 comprises three-dimensional coordinates and the orientation of mobile inspection device 112. The three-dimensional coordinates may be a Cartesian coordinate, a polar coordinate system or some other coordinate system that describes where mobile inspection device 112 is located with respect to vehicle 104. The position of mobile inspection device 112 may be identified by controller 128 using vehicle map 144 of vehicle 104.

The identification of position 132 may be performed in a number of different ways. For example, controller 128 may use simultaneous localization and mapping (SLAM) processes to track position 132 of mobile inspection device 112 operated by human operator 110 in real time. In other words, as position 132 changes, controller 128 may identify changes in position 132. A vehicle coordinate system for vehicle 104 may be used, or a coordinate system maybe generated on the fly during the movement of mobile inspection device 112 within vehicle 104 using simultaneous localization and mapping (SLAM) processes.

Controller 128 is configured to receive user input 124 comprising a group of gestures 134 made by human operator 110 with respect to item 136 in a group of items 138 in field of view 140 of mobile inspection device 112 based on position 132 of mobile inspection device 112. As depicted, field of view 140 is what mobile inspection device 112 is able to view and display based on position 132 of mobile inspection device 112. In this illustrative example, field of view 140 is what camera system 118 can generate images of, based on position 132 of mobile inspection device 112 with camera system 118.

Additionally, controller 128 is configured to create note 142 at location 152 with respect to vehicle 104 in association with item 136 in the group of items 138 in field of view 140 of mobile inspection device 112. Item 136 and the group of items 138 may take different forms. For example, items 138 may be selected from at least one of a seat, a carpet, a window, a door, an overhead storage bin, a light, an air duct, a monument, a rail, a skin panel, a wheel, a tire, an engine housing, a display device, a pump, or some other suitable type of item.

In the illustrative example, the different notes in inspection system 102 are electronic notes rather than physical notes. For example, note 142 is an electronic note. Note 142 is assigned to location 152. In other words, location 152 may be located in or on vehicle 104 in this illustrative example. Location 152 is a location within or on vehicle 104, and is described using three-dimensional coordinates.

In this illustrative example, note 142 is associated with item 136 by being marked or otherwise indicated in a database, record, or data structure, or as being for item 136. Location 152 may be the location of item 136 or a location near item 136.

In this illustrative example, note 142 may be generated during different times during the life cycle of vehicle 104. For example, note 142 may be generated during at least one of a final inspection prior to delivery to a customer, maintenance, an assembly of the vehicle, a certification of the vehicle, or some other time during the life cycle of vehicle 104.

Controller 128 is also configured to display note 142 in association with item 136 in field of view 140 on graphical user interface 122 on display system 116 for mobile inspection device 112. Note 142 is considered to be displayed in association with item 136 when the display of note 142 within graphical user interface 122 draws attention to item 136. For example, note 142 may be displayed on or in some proximate location to item 136, such that human operator 110 interprets note 142 as being for item 136.

In addition, controller 128 also may display notes 146 in addition to or in place of note 142. In this illustrative example, controller 128 is configured to identify a set of notes 146 in field of view 140 of mobile inspection device 112 for a current position of the mobile device and display the set of notes 146 on graphical user interface 122 on display system 116. As used herein, a "set" is zero or more of items 138. In other words, the set may be a null set in which none of items 138 are present or viewable. Controller 128 may identify the set of notes 146 on policy 148 applied to role 150 of human operator 110 of mobile inspection device 112. For example, items 138 may be present or a subset of items 138 may present in the set of items 138 based on role 150 of human operator 110.

In this illustrative example, policy 148 is one or more rules that may be used to identify which ones of items 138 in field of view 140 may be seen by a particular human operator. Role 150 of human operator 110 is an input into policy 148 in this illustrative example. Role 150 may be selected from an inspector, a reviewer, a data collector, a customer, a certifier, or some other type of role for a human operator.

In this manner, controller 128 provides a visualization to human operator 110 through mobile inspection device 112. For example, the display of note 142 in association with item 136 in field of view 140 on graphical user interface 122 on display system 116 for mobile inspection device 112 forms at least one of a mixed reality environment or an augmented reality environment for human operator 110.

Controller 128 may be implemented in software, hardware, firmware, or a combination thereof. When software is used, the operations performed by controller 128 may be implemented in program code configured to run on hardware, such as a processor unit. When firmware is used, the operations performed by controller 128 may be implemented in program code and data, and stored in a persistent memory to run on a processor unit. When hardware is employed, the hardware may include circuits that operate to perform the operations in controller 128.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components, and may be comprised entirely of organic components. For example, the processes may be implemented as circuits in organic semiconductors.

In one illustrative example, one or more technical solutions are present that overcome a technical problem with efficiently performing inspections in an aircraft. As a result, one or more technical solutions may provide a technical effect of creating notes in an electronic form in a mixed reality or an augmented reality display for inconsistencies that are more uniform and accurate, as compared to current techniques using physical notes.

As a result, mobile inspection device 112 operates as a special purpose computer system in which controller 128 in mobile inspection device 112 enables the inspecting of vehicle 104 to be performed more efficiently and accurately, as compared to current systems that employ physical notes. In particular, controller 128 transforms mobile inspection device 112 into a special purpose computer system, as compared to currently available general computer systems that do not have controller 128.

Figure 2:
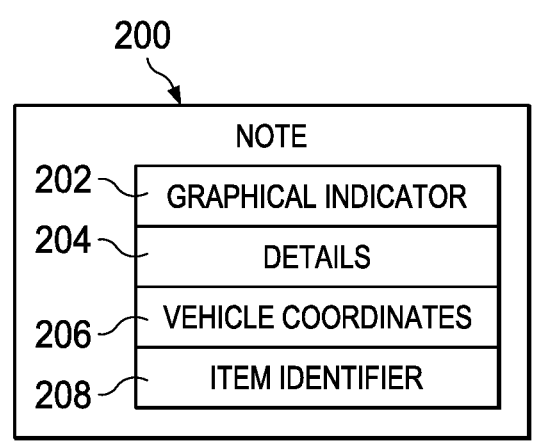
FIG. 2 is an illustration of a block diagram of a note in accordance with an illustrative embodiment.

With reference next to FIG. 2, an illustration of a block diagram of a note is depicted in accordance with an illustrative embodiment. Note 200 is an example of one implementation for notes 146 in FIG. 1. As depicted note 200 includes graphical indicator 202, details 204, vehicle coordinates 206, and item identifier 208.

In this illustrative example, graphical indicator 202 is displayed when note 200 is displayed in a graphical user interface. Graphical indicator 202 may take a number of different forms. For example, graphical indicator 202 may include at least one of an icon, an image, a widget, text, an animation, color, or some other type of indicator that may be displayed in the graphical user interface to point to or show an association with an item.

As depicted, details 204 include an explanation of an inconsistency. Details 204 include at least one of text, voice, an image, a video, or some other content that may be used to explain the inconsistency. The explanation may include a description of the inconsistency such as a scratch, a stain, a smudge, a part that does not work, an incorrect part, or some other type of description. The explanation also may include what corrective action is expected or other information.

In one illustrative example, details 204 may include voice annotations, in addition to or in place of text. For example, when the human operator is a customer representative making a final walk through prior to delivery of the aircraft, the voice annotations may be those of the customer representative. These voice annotations may reduce discrepancies in rework that may be performed.

As depicted, item identifier 208 identifies the item for which note 200 has been generated. Item identifier 208 may take various forms. For example, item identifier 208 may be a part number, a serial number, or some other type of identifier.

Further, graphical indicator 202 also may serve other functions, in addition to identifying an association with item identifier 208. In one illustrative example, graphical indicator 202 may be used to indicate a status of note 200. For example, graphical indicator 202 may indicate a status selected from a group consisting of new, in progress, and completed. The different statuses may be indicated through at least one of a color, an animation, an icon, or some other type of graphical indication.

As depicted, vehicle coordinates 206 identify the location for note 200 within or on vehicle 104 of FIG. 1. Vehicle coordinates 206 may be Cartesian coordinates, polar coordinates, or some other format based on a coordinate system for the vehicle. For example, the vehicle may have a vehicle map for which vehicle coordinates 206 describe a location within the vehicle using the coordinate system for the vehicle map. In this manner, note 200 is placed in a location relative to item identifier 208.

Figure 3:
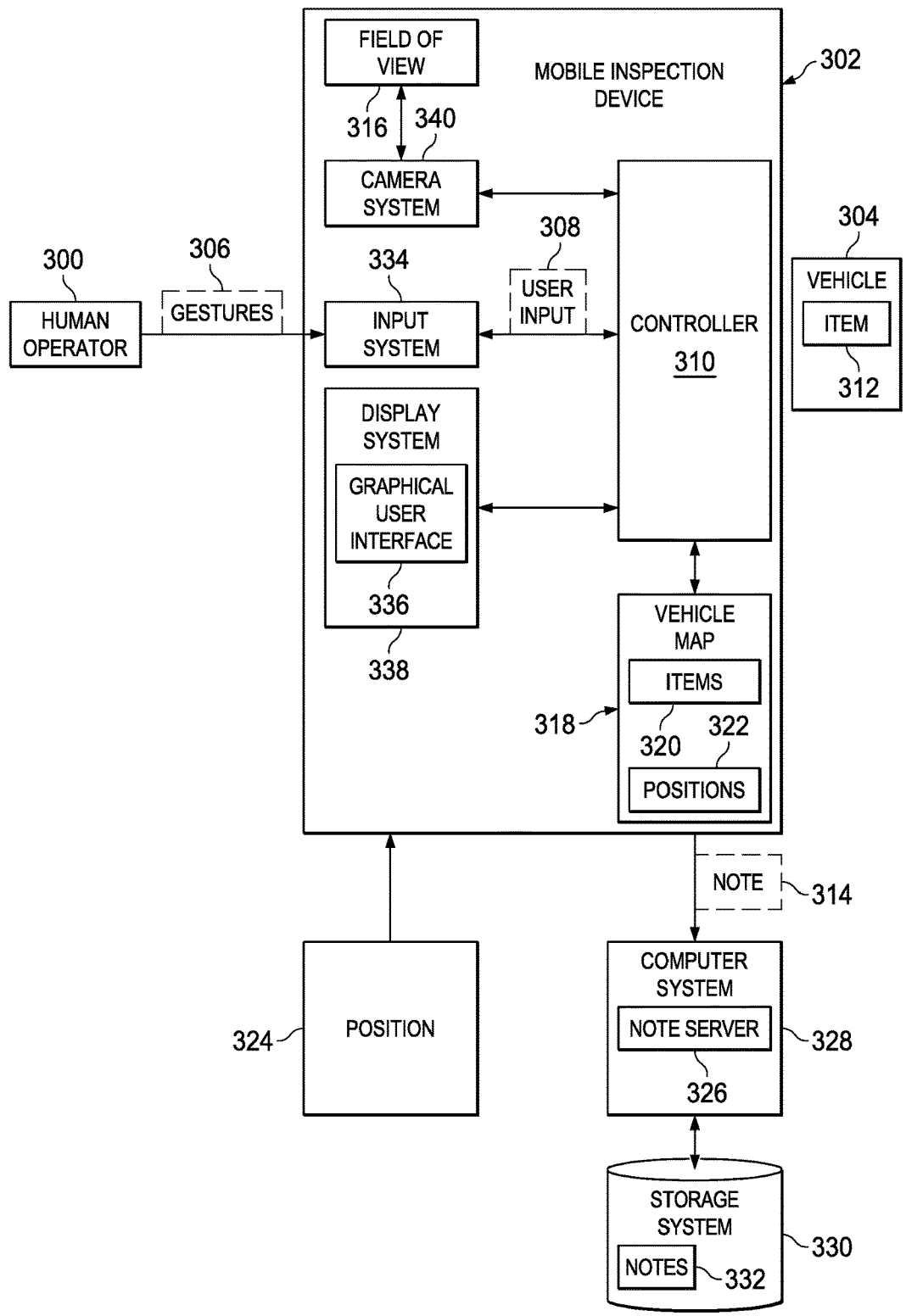
FIG. 3 is an illustration of a dataflow for creating notes in accordance with an illustrative embodiment.

With reference now to FIG. 3, an illustration of a dataflow for creating notes is depicted in accordance with an illustrative embodiment. In this depicted example, human operator 300 carries and operates mobile inspection device 302 to perform inspection of vehicle 304. Human operator 300 is a human operator in human operators 108 in FIG. 1 and mobile inspection device 302 is a mobile inspection device in the group of mobile inspection devices 154 in FIG. 1.

As depicted, controller 310 identifies position 324 of mobile inspection device 302 within vehicle 304. In other words, position 324 is shown in vehicle coordinates for vehicle 304, such that the location of mobile inspection device 302 operated by human operator 300 is known with respect to items 320 in vehicle 304.

As depicted, human operator 300 makes the group of gestures 306 that are detected by input system 334 to generate user input 308 for creating note 314. The group of gestures 306 may take various forms. For example, the group of gestures 306 may be the hand of human operator 300 touching item 312, covering item 312, moving across item 312, or some other movement within field of view 316 of mobile inspection device 302 as seen in graphical user interface 336 displayed on display system 338 for mobile inspection device 302.

The group of gestures 306 are received as user input 308 by controller 310 running on mobile inspection device 302. Controller 310 identifies item 312 in vehicle 304 based on the group of gestures 306. In other words, the group of gestures 306 may designate item 312 that is within field of view 316 of camera system 340 in mobile inspection device 302. The identification of item 312 may be made using vehicle map 318. In this illustrative example, vehicle map 318 contains items 320 and positions 322. Based on position 324 of mobile inspection device 302 and the group of gestures 306, item 312 in items 320 for vehicle 304 is identified as part of creating note 314.

As depicted, controller 310 for mobile inspection device 302 generates note 314. Note server 326 is located in computer system 328 and receives note 314 from controller 310.

Computer system 328 is a physical hardware system and includes one or more data processing systems. When more than one data processing system is present, the data processing systems are in communication with each other using a communications medium. The communications medium may be a network. The data processing systems may be selected from at least one of a computer, a server computer, a tablet, or some other suitable type of data processing system.

As depicted, note server 326 stores note 314 in storage system 330 with notes 332. Storage system 330 may take various forms. For example, storage system 330 may be comprised of at least one of a hard disk drive, a solid-state drive, a tape drive, an optical drive, or some other type of storage device. Storage system 330 may be in a single geographic location or distributed in different geographic locations.

In this manner, storage system 330 may store notes 332 in a history, enabling root cause analysis to reduce future inconsistencies. Controller 310 may display notes 332 for a group of locations over time for a group of vehicles, enabling viewing a trend of one or more inconsistencies in the location.

The illustration of inspection environment 100 in FIG. 1, and the different components in FIG. 1 and FIG. 2 are not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

For example, vehicle 104 may take other forms other than aircraft 106 in FIG. 1. For example, vehicle 104 may be selected from a group comprising a mobile platform, a surface ship, a tank, a personnel carrier, a train, a spacecraft, a submarine, a bus, an automobile, and some other suitable type of vehicle.

In another illustrative example, controller 128 may be distributed between mobile inspection device 112 and computer system 328 in FIG. 3. In other words, some of the processes in controller 128 may be implemented in mobile inspection device 112 and other processes may be implemented in computer system 328. In an alternate example, note server 326 may generate note 314 in response to receiving user input 308 generated by human operator 300 in FIG. 3.

As another example, a voice command or other type of input may be used in conjunction with the group of gestures 134 in FIG. 1 or the group of gestures 306 in FIG. 3. For example, a voice command to select an item while the hand of the human operator is pointing outward and touching an item may be used to designate the item as an item for which a note is to be created.

In another illustrative example, controller 128 in FIG. 1 or controller 310 in FIG. 3 may display notes for a group of locations over time for a group of vehicles, enabling viewing a trend of one or more inconsistencies in the location.

In another example, controller 128 or controller 310 may display a group of metrics for the group of items 138 in FIG. 1 or items 320 in FIG. 3. Further, controller 128 or controller 310 may facilitate communication with a group of remote experts. Further, controller 128 or controller 310 may display a group of metrics for the group of items. The group of metrics may indicate a standard or specification for which an item should meet.

Figure 4:
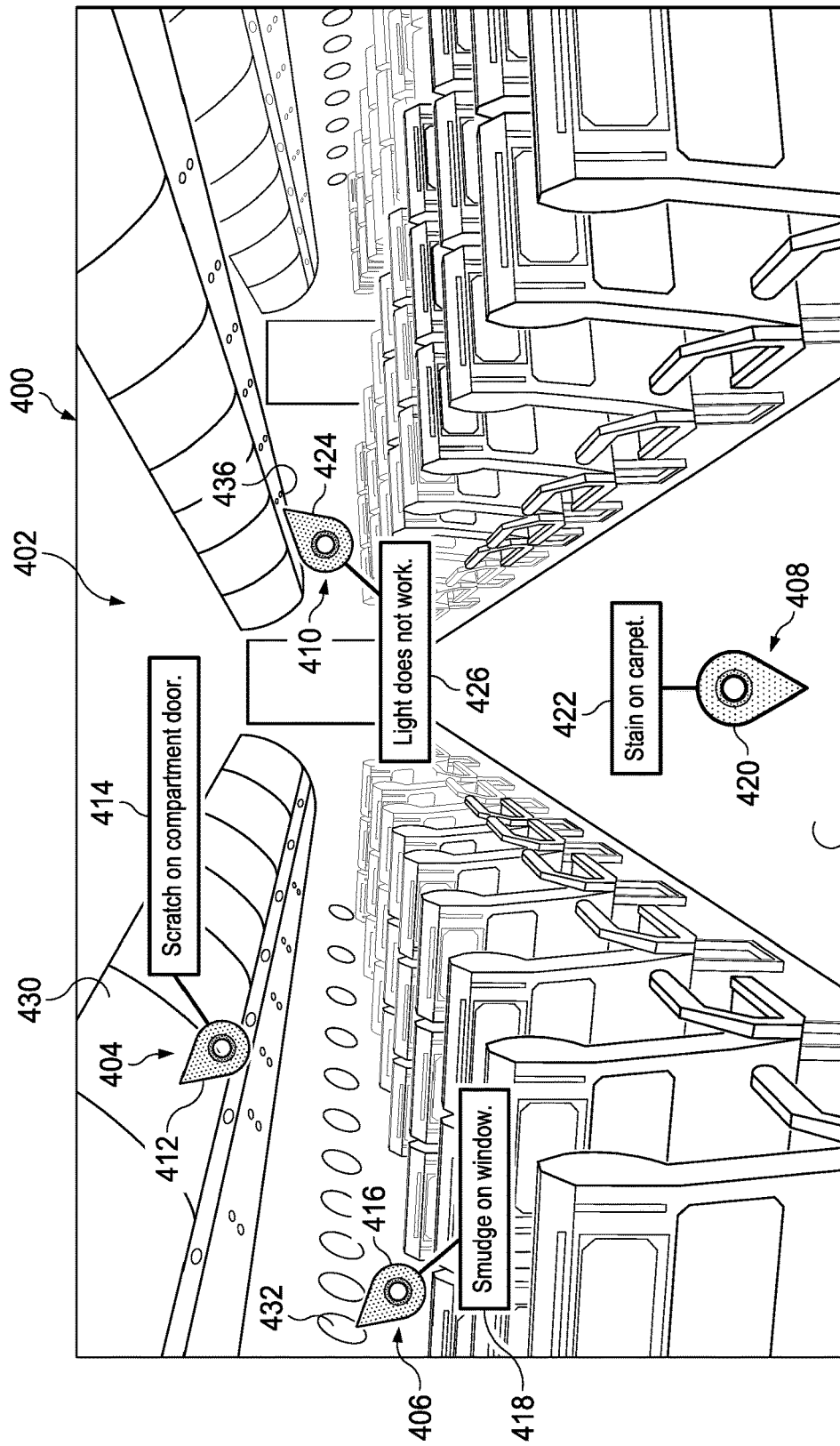
FIG. 4 is an illustration of notes displayed in a graphical user interface in accordance with an illustrative embodiment.

With reference now to FIG. 4, an illustration of notes displayed in a graphical user interface is depicted in accordance with an illustrative embodiment. In this illustrative example, graphical user interface 400 is an example of an implementation for graphical user interface 122 in FIG. 1 and graphical user interface 336 in FIG. 3. In this example, graphical user interface 400 is displayed from a mobile inspection device, such as a pair of smart glasses.

In this illustrative example, an augmented reality view of passenger cabin 402 is shown in graphical user interface 400. Passenger cabin 402 is shown using images generated by a camera system in the smart glasses. Additionally, notes are displayed in graphical user interface 400. In particular, graphical user interface 400 includes note 404, note 406, note 408, and note 410.

These notes are displayed in association with items. For example, note 404 is displayed in association with overhead bin 430. Note 406 is displayed in association with window 432. Note 408 is displayed in association with carpet 434. Note 410 is displayed in association with light 436. These notes augment the display of the physical items shown in graphical user interface 400 to provide an augmented reality for a human operator.

Each of these notes includes a graphical indicator and details. For example, note 404 includes graphical indicator 412 and details 414. Note 406 includes graphical indicator 416 and details 418. Note 408 includes graphical indicator 420 and details 422. Note 410 includes graphical indicator 424 and details 426.

Figure 5:
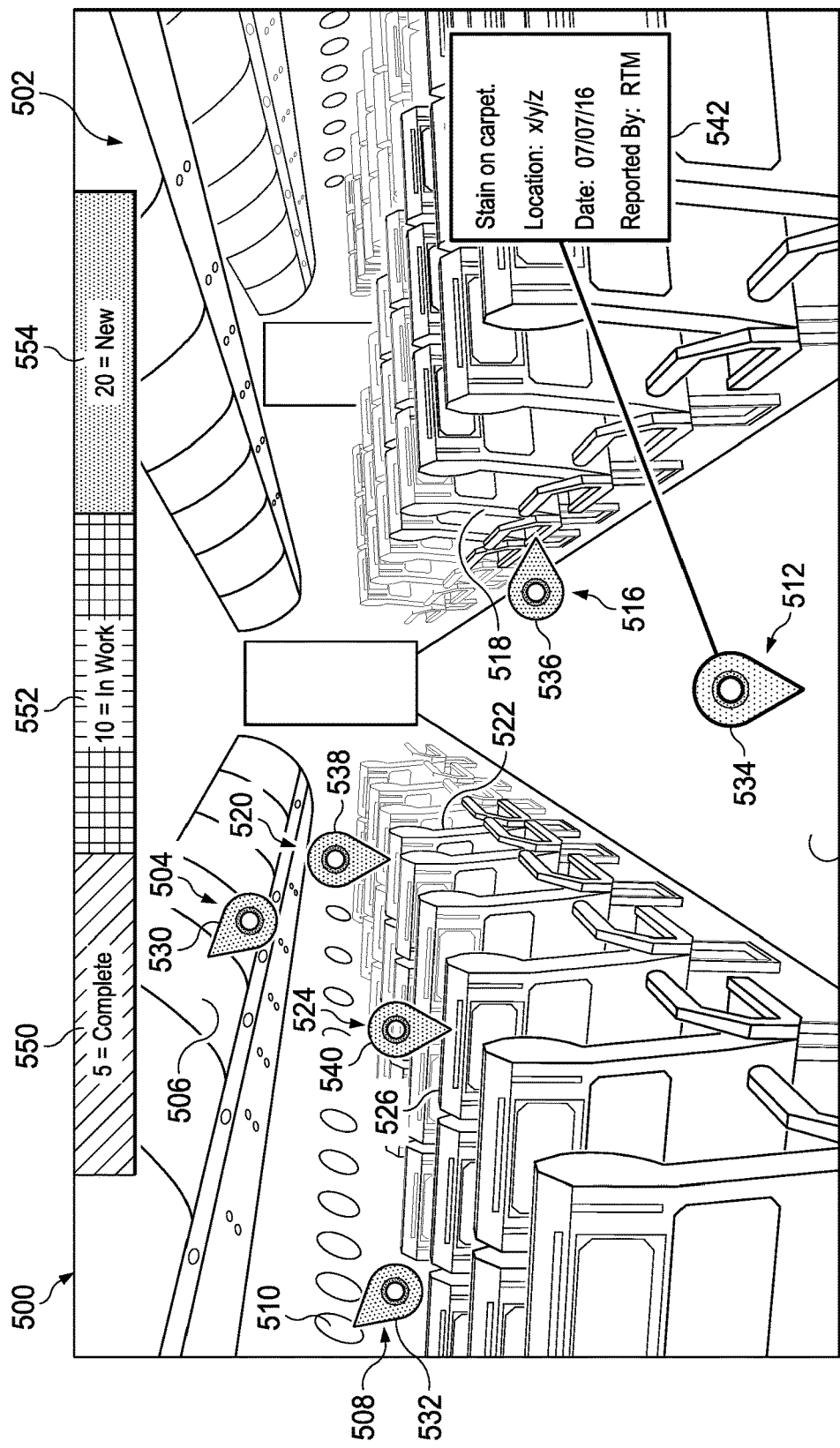
FIG. 5 is an illustration of notes displayed in a graphical user interface in accordance with an illustrative embodiment.

With reference now to FIG. 5, an illustration of notes displayed in a graphical user interface is depicted in accordance with an illustrative embodiment. In this illustrative example, graphical user interface 500 is an example of an implementation for graphical user interface 122 in FIG. 1 and graphical user interface 336 in FIG. 3. In this example, graphical user interface 500 is displayed from a mobile inspection device, such as a pair of smart glasses.

As depicted, graphical user interface 500 also provides an augmented reality display of passenger cabin 502. In this illustrative example, notes are displayed in conjunction with items in passenger cabin 502. For example, note 504 is displayed for overhead bin 506, and note 508 is displayed for window 510. Note 512 is displayed for carpet 514. As depicted, note 516 is displayed for seat 518, note 520 is displayed for seat 522, and note 524 is displayed for seat 526.

In this example, note 504 has graphical indicator 530, note 508 has graphical indicator 532, note 512 has graphical indicator 534, note 516 has graphical indicator 536, note 520 has graphical indicator 538, and note 524 has graphical indicator 540. As depicted, graphical indicator 534 has been selected causing details 542 to be displayed for note 512.

Additionally, graphical user interface 500 also display status information about the notes. Section 550 indicates notes for work that has been completed, section 552 indicates notes for work that are in progress, and section 554 indicates notes that are new in which work has not yet been started. Further, each of the sections are color coded to correspond with the colors for the graphical indicators.

As a result, in addition to seeing the status for the notes, the status of individual notes may be identified from the colors of the graphical indicators. For example, note 504, note 508, note 512, note 516, note 520, and note 524 are new notes in which work has not yet been started.

Figure 6:
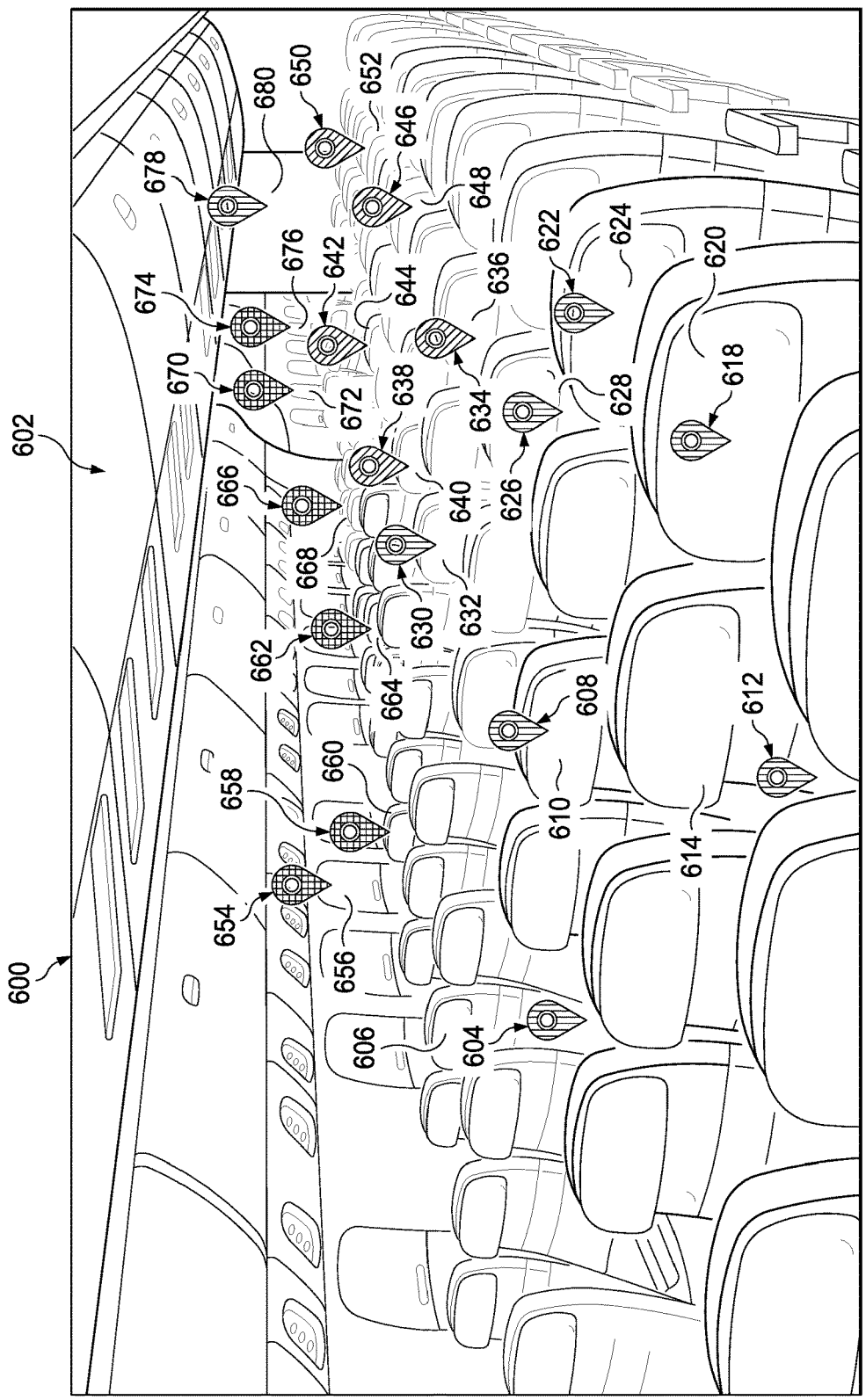
FIG. 6 is an illustration of notes displayed in a graphical user interface in accordance with an illustrative embodiment.

Turning to FIG. 6, an illustration of notes displayed in a graphical user interface is depicted in accordance with an illustrative embodiment. In this illustrative example, graphical user interface 600 is an example of an implementation for graphical user interface 122 in FIG. 1 and graphical user interface 336 in FIG. 3. In this example, graphical user interface 600 is displayed from a mobile inspection device, such as a pair of smart glasses.

As depicted, a view of passenger cabin 602 is seen in graphical user interface 600. In this illustrative example, notes are displayed using graphical indicators that are overlaid on a view of passenger cabin 602 as seen by the human operator on graphical user interface 600.

In this illustrative example, the notes include note 604 on passenger seat 606, note 608 on passenger seat 610, note 612 on passenger seat 614, note 618 on passenger seat 620, note 622 on passenger seat 624, note 626 on passenger seat 628, note 630 on passenger seat 632, note 634 on passenger seat 636, note 638 on passenger seat 640, note 642 on passenger seat 644, note 646 on passenger seat 648, note 650 on passenger seat 652, note 658 on passenger seat 660, note 662 on passenger seat 664, and note 666 on passenger seat 668. The notes also include note 654 on window 656, note 670 on window 672, note 674 on window 676. Note 678 is on wall 680 in this example.

Figure 7:
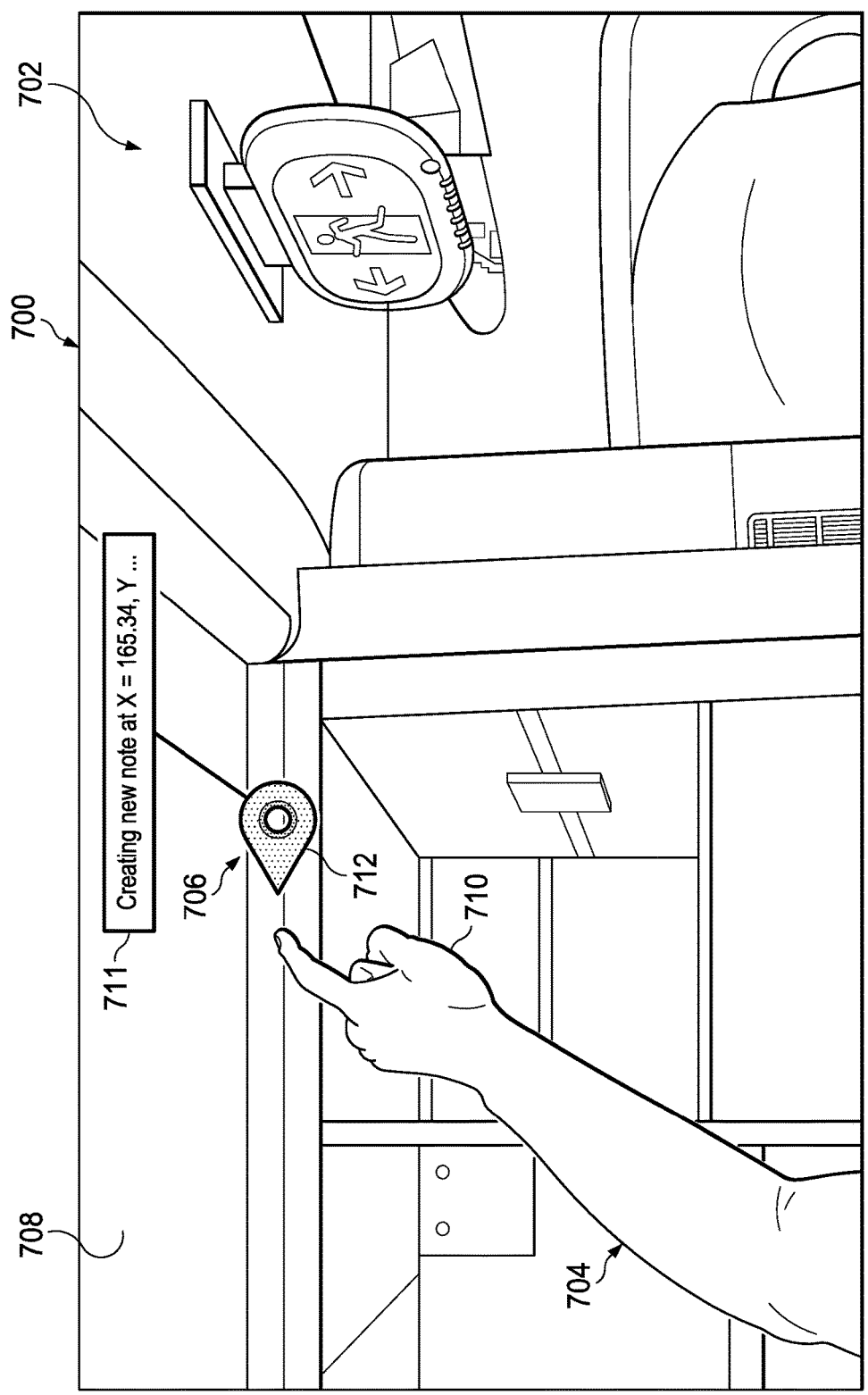
FIG. 7 is an illustration of the creation of a note in a graphical user interface in accordance with an illustrative embodiment.

With reference now to FIG. 7, an illustration of the creation of a note in a graphical user interface is depicted in accordance with an illustrative embodiment. In this illustrative example, graphical user interface 700 is an example of an implementation for graphical user interface 122 in FIG. 1 and graphical user interface 336 in FIG. 3. In this example, graphical user interface 700 is displayed from a mobile inspection device, such as a pair of smart glasses.

As depicted, a view of passenger cabin 702 is shown in graphical user interface 700. In this illustrative example, human operator 704 has created note 706 for ceiling 708. As depicted, human operator 704 has made a gesture by pointing to ceiling 708 with hand 710. Additionally, human operator 704 has uttered a command, such as "create note", in addition to the gesture of pointing to ceiling 708.

In response to the gesture, graphical indicator 712 is created and displayed for note 706 pointing towards ceiling 708. Additionally, human operator 704 may also add details in details 711. These details may be voice notes, text, an image of ceiling 708, or other suitable details to indicate the presence of an inconsistency in ceiling 708.

The illustration of the graphical user interfaces in FIGS. 4-6 are examples of some implementations for graphical user interface 122 shown in block form in FIG. 1 and graphical user interface 336 shown in block form in FIG. 3. These illustrations are only meant as examples and not meant to limit the manner in which graphical user interface 122 and graphical user interface 336 may be implemented in other examples. For example, an animation or other type of icon may be used, in addition to or in place of the ones shown, in these figures. Further, different types of graphical indicators may be used in the same graphical user interface. In other words, the graphical indicators displayed in graphical user interfaces may be heterogeneous in composition. Different graphical indicators may be used to indicate different types of items. For example, a first type of graphical indicator may be used to indicate a passenger seat, a second type of graphical indicator may be to indicate a window, and a third type of graphical indicator may be used to indicate a stowage.

Figure 8:
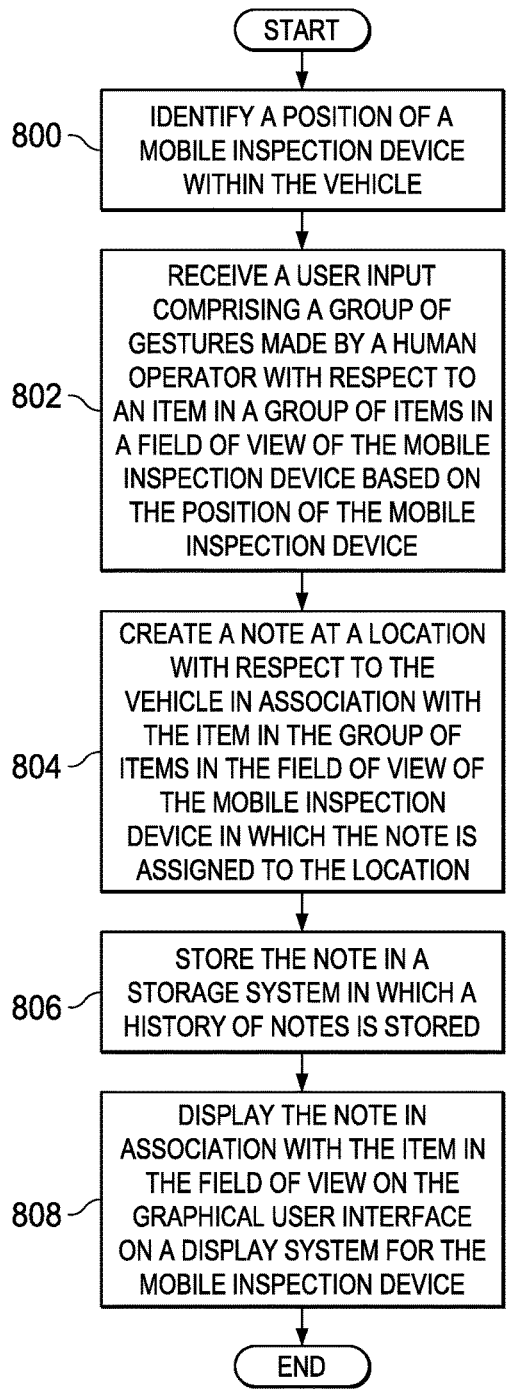
FIG. 8 is an illustration of a flowchart of a process for inspecting a vehicle in accordance with an illustrative embodiment.

Turning next to FIG. 8, a flowchart of a process for inspecting a vehicle is depicted in accordance with an illustrative embodiment. The process illustrated in FIG. 8 may be implemented in inspection system 102 in FIG. 1. As depicted, the different operations may be implemented in controller 128 in FIG. 1 or controller 310 in FIG. 3. These operations may be implemented as program code that is processed by a processing unit in a data processing system.

The process begins by identifying a position of a mobile inspection device within the vehicle (operation 800). The process receives a user input comprising a group of gestures made by a human operator with respect to an item in a group of items in a field of view of the mobile inspection device based on the position of the mobile inspection device (operation 802).

The process creates a note at a location with respect to the vehicle in association with the item in the group of items in the field of view of the mobile inspection device in which the note is assigned to the location (operation 804). The process stores the note in a storage system in which a history of notes is stored (operation 806).

The process displays the note in association with the item in the field of view on the graphical user interface on a display system for the mobile inspection device (operation 808). The process terminates thereafter.

Figure 9:
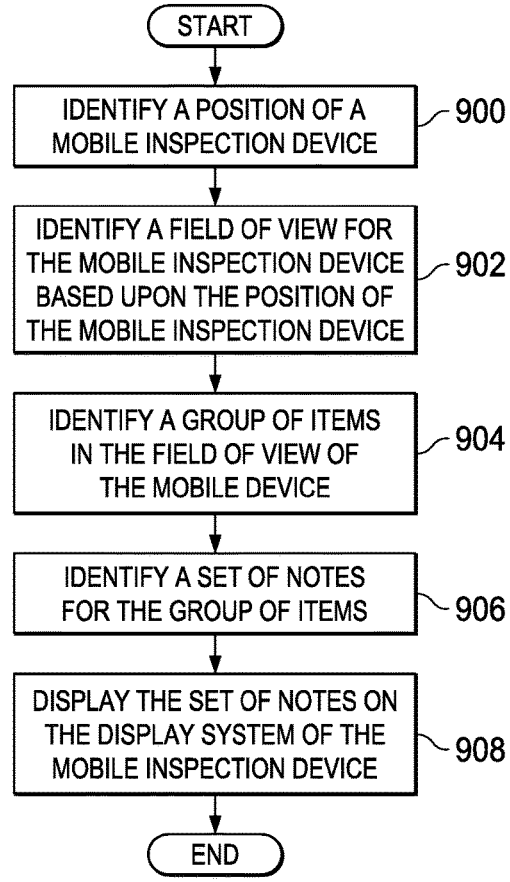
FIG. 9 is an illustration of a flowchart of a process for displaying notes in accordance with an illustrative embodiment.

With reference now to FIG. 9, a flowchart of a process for displaying notes is depicted in accordance with an illustrative embodiment. The operations in the process illustrated in FIG. 9 may be implemented as program code, hardware or some combination thereof in controller 128 in FIG. 1 or controller 310 in FIG. 3.

The process begins by identifying a position of a mobile inspection device (operation 900). The process identifies a field of view for the mobile inspection device based upon the position of the mobile inspection device (operation 902). In this illustrative example, the field of view is based on what the mobile inspection device is able to display on a display system.

The process identifies a group of items in the field of view of the mobile device (operation 904). The process identifies a set of notes for the group of items (operation 906). As depicted, the set of notes may be a null set in which no notes are present for the group of items in the field of view.

The process displays the set of notes on the display system of the mobile inspection device (operation 908). The process terminates thereafter. This process may be repeated any number of times as the position of the mobile inspection device changes.

Figure 10:
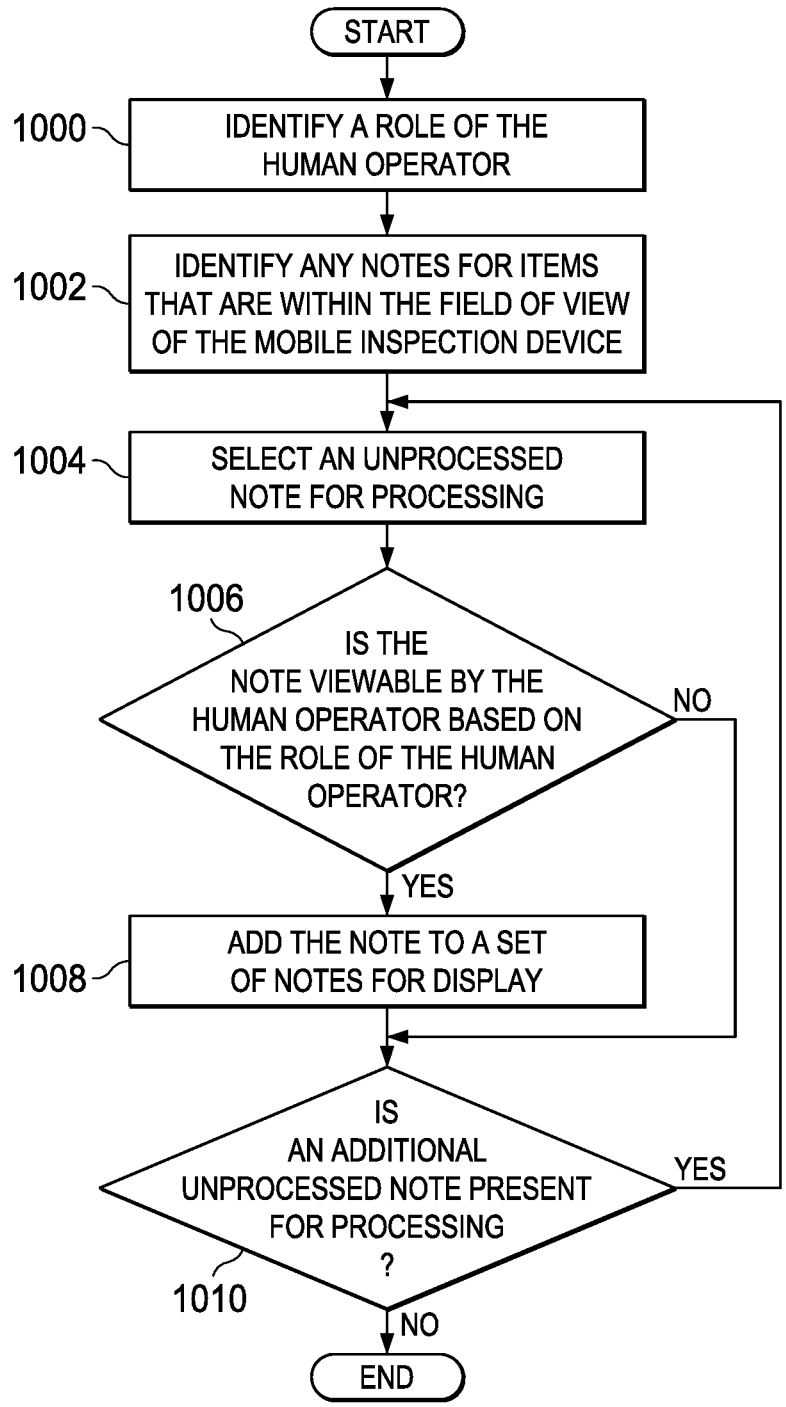
FIG. 10 is an illustration of a flowchart of a process for identifying notes displayable based on the role of a human operator in accordance with an illustrative embodiment.

With reference now to FIG. 10, a flowchart of a process for identifying notes displayable based on the role of a human operator is depicted in accordance with an illustrative embodiment. The operations in the process illustrated in FIG. 10 may be implemented as program code, hardware or some combination thereof in controller 128 in FIG. 1 or controller 310 in FIG. 3. The operations in this flowchart are an example of one manner in which operation 906 in FIG. 9 may be implemented.

The process begins by identifying a role of the human operator (operation 1000). The process identifies any notes for items that are within the field of view of the mobile inspection device (operation 1002). The process selects an unprocessed note for processing (operation 1004).

The process determines whether the note is viewable by the human operator based on the role of the human operator (operation 1006). Each note may have an identification of what roles may or may not view a particular note. The determination may be made using mechanisms, such as access control lists or other types of policies or mechanisms. For example, policy 148 in FIG. 1 may be used to determine what notes may be viewed by a human operator.

If the note is viewable by the human operator based on the role of the human operator, the note is added to a set of notes for display (operation 1008). The process then determines whether an additional unprocessed note is present for processing (operation 1010). If an additional unprocessed note is present, the process returns to operation 1004. Otherwise, the process terminates with a set of notes being created for display. With reference again to operation 1006, if the note is not viewable, the process proceeds to operation 1010 as described above. In this manner, the notes generated by the human operator of the mobile inspection device and notes generated by other human operators may view the notes for a vehicle.

Figure 11:
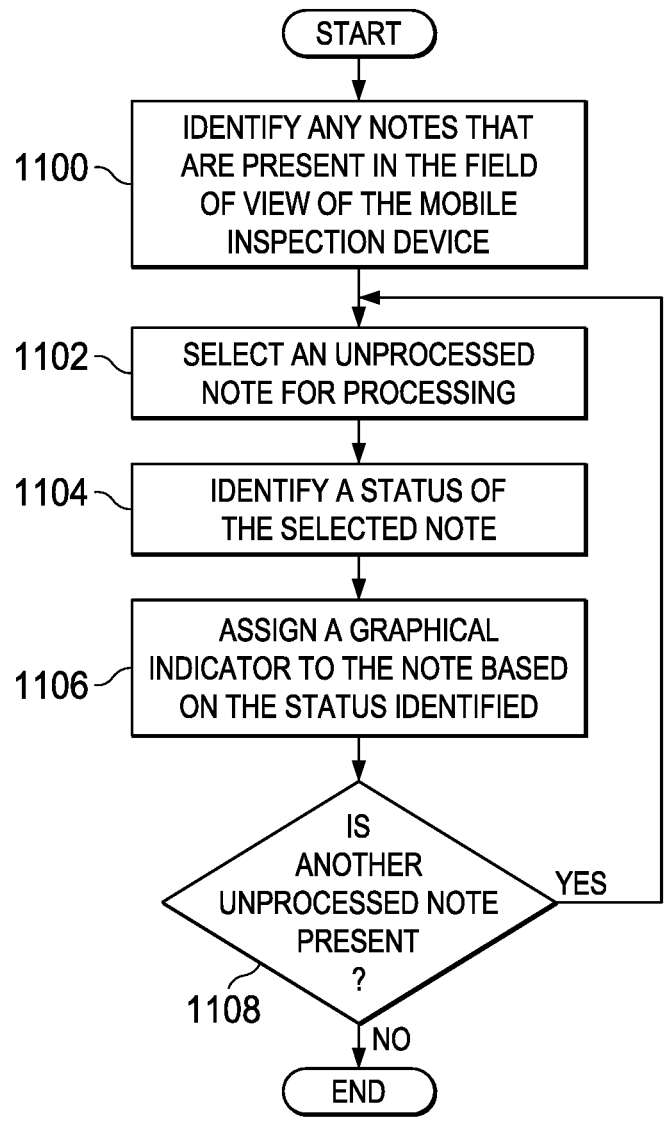
FIG. 11 is an illustration of a flowchart of a process for identifying notes displayable based on the status of a note in accordance with an illustrative embodiment.

With reference now to FIG. 11, a flowchart of a process for identifying notes displayable based on the status of a note is depicted in accordance with an illustrative embodiment. The operations in the process illustrated in FIG. 11 may be implemented as program code, hardware or some combination thereof in controller 128 in FIG. 1 or controller 310 in FIG. 3. The operations in this flowchart are an example of one manner in which operation 906 in FIG. 9 may be implemented.

The process begins by identifying any notes that are present in the field of view of the mobile inspection device (operation 1100). The process selects an unprocessed note for processing (operation 1102). The process identifies a status of the selected note (operation 1104). The note may have different types of statuses depending on the implementation. For example, the status maybe selected from at least one of new, completed, or in progress.

The process assigns a graphical indicator to the note based on the status identified (operation 1106). The graphical indicator is selected to indicate the status of the note. For example, a color, text, an icon, an animation, or a graphic may be selected to indicate the status of the note.

A determination is made as to whether another unprocessed note is present (operation 1108). If another unprocessed note is present, the process returns to operation 1102. Otherwise, the process terminates.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added, in addition to the illustrated blocks, in a flowchart or block diagram.

Figure 12:
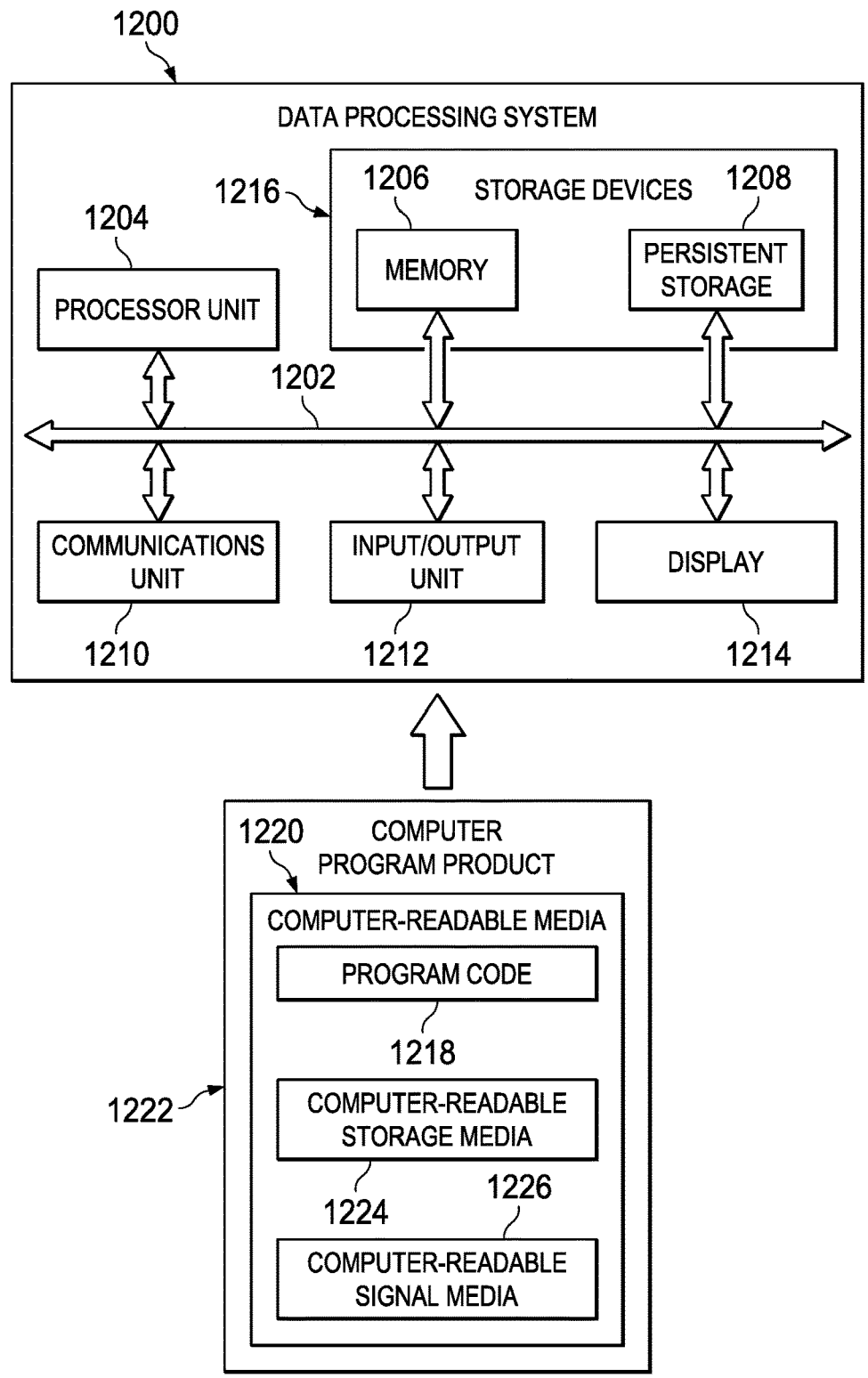
FIG. 12 is an illustration of a block diagram of a data processing system in accordance with an illustrative embodiment.

Turning now to FIG. 12, an illustration of a block diagram of a data processing system is depicted in accordance with an illustrative embodiment. Data processing system 1200 may be used to implement mobile inspection device 112 in FIG. 1, mobile inspection device 302 in FIG. 3, and one or more computers in computer system 328 in FIG. 3. In this illustrative example, data processing system 1200 includes communications framework 1202, which provides communications between processor unit 1204, memory 1206, persistent storage 1208, communications unit 1210, input/output unit 1212, and display 1214. In this example, communications framework 1202 may take the form of a bus system.

Processor unit 1204 serves to execute instructions for software that may be loaded into memory 1206. Processor unit 1204 may be a number of processors, a multi-processor core, or some other type of processor, depending on the particular implementation.

Memory 1206 and persistent storage 1208 are examples of storage devices 1216. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1216 may also be referred to as computer-readable storage devices in these illustrative examples. Memory 1206, in these examples, may be, for example, a random-access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a solid state hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these illustrative examples, provides for communications with other data processing systems or devices. In these illustrative examples, communications unit 1210 is a network interface card.

Input/output unit 1212 allows for input and output of data with other devices that may be connected to data processing system 1200. For example, input/output unit 1212 may provide a connection for user input through at least one of a keyboard, a mouse, or some other suitable input device. Further, input/output unit 1212 may send output to a printer. Display 1214 provides a mechanism to display information to a user.

Instructions for at least one of the operating system, applications, or programs may be located in storage devices 1216, which are in communication with processor unit 1204 through communications framework 1202. The processes of the different embodiments may be performed by processor unit 1204 using computer-implemented instructions, which may be located in a memory, such as memory 1206.

These instructions are referred to as program code, computer-usable program code, or computer-readable program code that may be read and executed by a processor in processor unit 1204. The program code in the different embodiments may be embodied on different physical or computer-readable storage media, such as memory 1206 or persistent storage 1208.

Program code 1218 is located in a functional form on computer-readable media 1220 that is selectively removable and may be loaded onto or transferred to data processing system 1200 for execution by processor unit 1204. Program code 1218 and computer-readable media 1220 form computer program product 1222 in these illustrative examples. In one example, computer-readable media 1220 may be computer-readable storage media 1224 or computer-readable signal media 1226.

In these illustrative examples, computer-readable storage media 1224 is a physical or tangible storage device used to store program code 1218 rather than a medium that propagates or transmits program code 1218. Alternatively, program code 1218 may be transferred to data processing system 1200 using computer-readable signal media 1226. Computer-readable signal media 1226 may be, for example, a propagated data signal containing program code 1218. For example, computer-readable signal media 1226 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1200 are not meant to provide architectural limitations to the manner in which different embodiments may be implemented. The different illustrative embodiments may be implemented in a data processing system including components, in addition to or in place of those illustrated, for data processing system 1200. Other components shown in FIG. 12 can be varied from the illustrative examples shown. The different embodiments may be implemented using any hardware device or system capable of running program code 1218.

Figure 13:
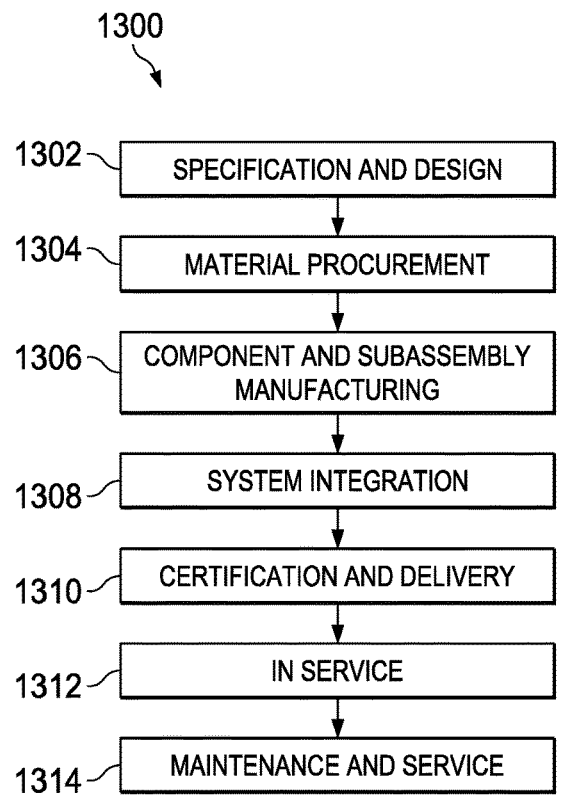
FIG. 13 is an illustration of a block diagram of an aircraft manufacturing and service method in accordance with an illustrative embodiment.
Figure 14:
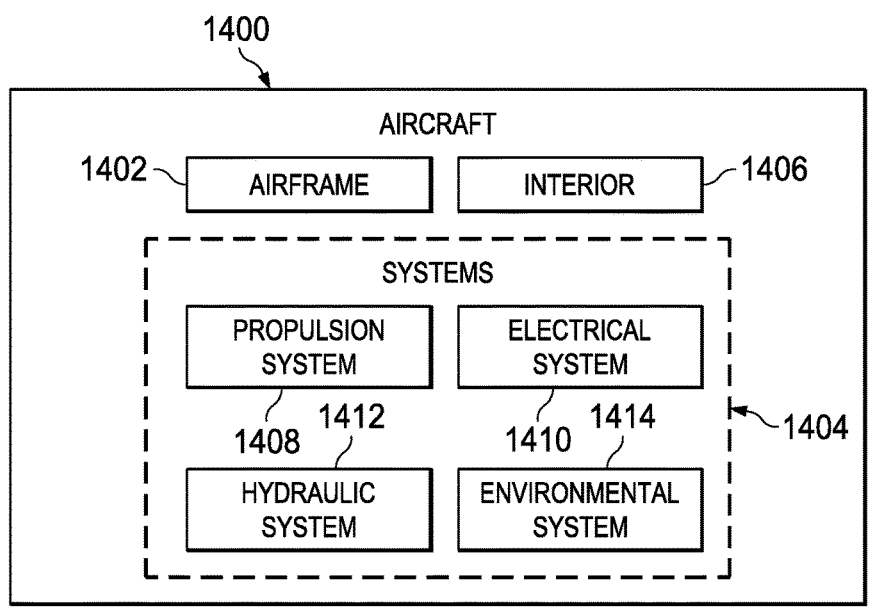
FIG. 14 is an illustration of a block diagram of an aircraft in which an illustrative embodiment may be implemented.

The illustrative embodiments of the present disclosure may be described in the context of aircraft manufacturing and service method 1300 as shown in FIG. 13 and aircraft 1400 as shown in FIG. 14. Turning first to FIG. 13, an illustration of a block diagram of an aircraft manufacturing and service method is depicted in accordance with an illustrative embodiment. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 in FIG. 14 takes place. Thereafter, aircraft 1400 in FIG. 14 may go through certification and delivery 1310 in order to be placed in service 1312. While in service 1312 by a customer, aircraft 1400 in FIG. 14 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of a block diagram of an aircraft is depicted in which an illustrative embodiment may be implemented. In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. For example, one or more illustrative examples may be implemented during system integration 1308 or certification and delivery 1310 to perform inspections of aircraft 1400.

In one illustrative example, components or subassemblies produced in component and subassembly manufacturing 1306 in FIG. 13 may be fabricated or manufactured in a manner similar to components or subassemblies produced while aircraft 1400 is in service 1312 in FIG. 13. As yet another example, one or more apparatus embodiments, method embodiments, or a combination thereof may be utilized during the production stages, such as component and subassembly manufacturing 1306 and system integration 1308 in FIG. 13. One or more apparatus embodiments, method embodiments, or a combination thereof may be utilized while aircraft 1400 is in service 1312, during maintenance and service 1314 in FIG. 13, or both.

The use of a number of the different illustrative embodiments may substantially expedite the assembly of aircraft 1400, reduce the cost of aircraft 1400, or both expedite the assembly of aircraft 1400 and reduce the cost of aircraft 1400. With the ability to visualize items with inconsistencies that needs reworking, the illustrative examples provide a more efficient system for creating notes and identifying items for those notes as compared to currently used systems that perform physical marking of the items in aircraft 1400.

Figure 15:
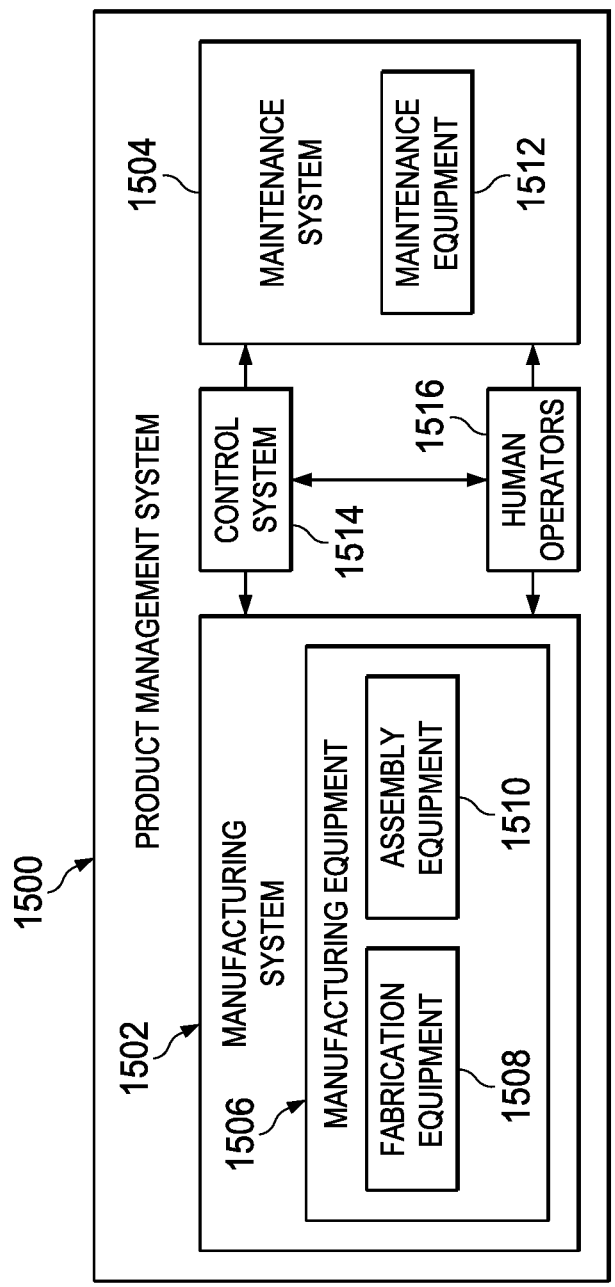
FIG. 15 is an illustration of a block diagram of a product management system in accordance with an illustrative embodiment.

Turning now to FIG. 15, an illustration of a block diagram of a product management system is depicted in accordance with an illustrative embodiment. Product management system 1500 is a physical hardware system. In this illustrative example, product management system 1500 may include at least one of manufacturing system 1502 or maintenance system 1504.

Manufacturing system 1502 is configured to manufacture products, such as aircraft 1400 in FIG. 14. As depicted, manufacturing system 1502 includes manufacturing equipment 1506. Manufacturing equipment 1506 includes at least one of fabrication equipment 1508 or assembly equipment 1510.

Fabrication equipment 1508 is equipment that may be used to fabricate components for parts used to form aircraft 1400. For example, fabrication equipment 1508 may include machines and tools. These machines and tools may be at least one of a drill, a hydraulic press, a furnace, a mold, a composite tape laying machine, a vacuum system, a lathe, or other suitable types of equipment. Fabrication equipment 1508 may be used to fabricate at least one of metal parts, composite parts, semiconductors, circuits, fasteners, ribs, skin panels, spars, antennas, or other suitable types of parts.

Assembly equipment 1510 is equipment used to assemble parts to form aircraft 1400. In particular, assembly equipment 1510 may be used to assemble components and parts to form aircraft 1400. Assembly equipment 1510 also may include machines and tools. These machines and tools may be at least one of a robotic arm, a crawler, a faster installation system, a rail-based drilling system, or a robot. Assembly equipment 1510 may be used to assemble parts such as seats, horizontal stabilizers, wings, engines, engine housings, landing gear systems, and other parts for aircraft 1400.

In this illustrative example, maintenance system 1504 includes maintenance equipment 1512. Maintenance equipment 1512 may include any equipment needed to perform maintenance on aircraft 1400. Maintenance equipment 1512 may include tools for performing different operations on parts on aircraft 1400. These operations may include at least one of disassembling parts, refurbishing parts, inspecting parts, reworking parts, manufacturing replacement parts, or other operations for performing maintenance on aircraft 1400. These operations may be for routine maintenance, inspections, upgrades, refurbishment, or other types of maintenance operations.

In the illustrative example, maintenance equipment 1512 may include ultrasonic inspection devices, x-ray imaging systems, vision systems, drills, crawlers, and other suitable devices. In some cases, maintenance equipment 1512 may include fabrication equipment 1508, assembly equipment 1510, or both, to produce and assemble parts that may be needed for maintenance.

Product management system 1500 also includes control system 1514. Control system 1514 is a hardware system and may also include software or other types of components. Control system 1514 is configured to control the operation of at least one of manufacturing system 1502 or maintenance system 1504. In particular, control system 1514 may control the operation of at least one of fabrication equipment 1508, assembly equipment 1510, or maintenance equipment 1512.

The hardware in control system 1514 may be using hardware that may include computers, circuits, networks, and other types of equipment. The control may take the form of direct control of manufacturing equipment 1506. For example, robots, computer-controlled machines, and other equipment may be controlled by control system 1514. In other illustrative examples, control system 1514 may manage operations performed by human operators 1516 in manufacturing or performing maintenance on aircraft 1400. For example, control system 1514 may assign tasks, provide instructions, display models, or perform other operations to manage operations performed by human operators 1516. In these illustrative examples, note server 326 in FIG. 3 may be implemented in control system 1514 to manage at least one of the manufacturing or maintenance of aircraft 1400 in FIG. 14.

In the illustrative example, note server 326 also may operate to schedule work orders for inconsistencies that have been identified by a controller and a mobile inspection device. In these illustrative examples, the notes may be used to generate work orders. In other illustrative examples, the notes may be generated in the form of work orders that may be scheduled for performance within product management system 1500.

For example, note server 326 also may identify trends, or output other information that may be used to control the operation of at least one of manufacturing equipment 1506 or assembly equipment 1510. For example, selections of particular equipment or the scheduling and maintenance for equipment may be performed based on the identification of inconsistencies.

In the different illustrative examples, human operators 1516 may operate or interact with at least one of manufacturing equipment 1506, maintenance equipment 1512, or control system 1514. This interaction may be performed to manufacture aircraft 1400.

Of course, product management system 1500 may be configured to manage other products other than aircraft 1400. Although product management system 1500 has been described with respect to manufacturing in the aerospace industry, product management system 1500 may be configured to manage products for other industries. For example, product management system 1500 may be configured to manufacture products for the automotive industry as well as any other suitable industries.

Thus, the illustrative examples provide one or more technical solutions in which the amount of time needed between identifying an inconsistency to when an inconsistency is remedied may be reduced, as compared to currently used techniques. One or more technical solutions are present in which the generation of electronic notes and the processing of electronic notes enables faster processing, and more consistency in resolving inconsistencies in vehicles, such as an aircraft. Additionally, one or more technical solutions provide a technical effect in which root cause analysis may be made more easily from the notes, as compared to current processes.

One or more illustrative examples may provide a technical solution in which the management of a product during at least one of manufacturing or maintenance may be performed more efficiently as compared to currently available techniques using paper notes. In one or more illustrative examples, the technical solutions present in which work orders may be generated, scheduled, or both generated and scheduled based on the notes.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. For example, other illustrative embodiments may be applied to other applications in addition to or in place of inspecting vehicles. For example, one illustrative example may be applied to inspecting a home. Customer walk-throughs for final approval may be performed using inspection system 102 in FIG. 1. As another example, an inspection of mobile platforms, stationary platforms, land-based structures, aquatic-based structures, space-based structures, or other types of platforms may be performed using inspection system 102 in FIG. 1. These platforms may include, for example, a building, a manufacturing facility, a dam, a space station, or other type of platform.

Another application of an illustrative embodiment may be applied for inspecting patients at medical appointments. For example, a doctor may examine a patient and see that the patient's tonsils are swollen. The doctor may use inspection system 102 in FIG. 1 to create an image of the tonsils and enter information about the tonsils to create a note while looking at the tonsils. This information may then be added to the file for the patient.

The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A vehicle inspection system comprising:
    a mobile inspection device;
    a display system for the mobile inspection device;
    a graphical user interface configured to be displayed on the display system; and
    a controller configured to operate with the mobile inspection device, wherein the controller is configured to identify a position of the mobile inspection device within a vehicle; receive a user input comprising a group of gestures made by a human operator with respect to an item in a group of items in a field of view of the mobile inspection device based on the position of the mobile inspection device; create a note at a location with respect to the vehicle in association with the item in the field of view of the mobile inspection device in which the note is assigned to the location with respect to the vehicle; and display the note in association with the item in the field of view on the graphical user interface on the display system for the mobile inspection device.

2. The vehicle inspection system of claim 1 further comprising:
    a storage system in which a history of notes is stored.

3. The vehicle inspection system of claim 1, wherein the controller is configured to identify a set of notes in the field of view of the mobile inspection device for a current position of the mobile inspection device and display the set of notes on the graphical user interface on the display system.

4. The vehicle inspection system of claim 3, wherein the set of notes identified is based on a policy applied to a role of the human operator of the mobile inspection device.

5. The vehicle inspection system of claim 1, wherein the controller is located in at least one of the mobile inspection device or a remote computer in communication with the mobile inspection device.

6. The vehicle inspection system of claim 1, wherein the display of the note in association with the item in the field of view on the graphical user interface on the display system for the mobile inspection device forms at least one of a mixed reality environment or an augmented reality environment.

7. The vehicle inspection system of claim 1, wherein the note comprises a graphical indicator and details selected from at least one of text, voice, an image, or a video.

8. The vehicle inspection system of claim 7, wherein the graphical indicator indicates a status selected from a group consisting of new, in progress, and completed.

9. The vehicle inspection system of claim 1, wherein the controller stores notes for the vehicle in a history, enabling root cause analysis to reduce future inconsistencies.

10. The vehicle inspection system of claim 1, wherein the controller displays notes for a group of locations over time for a group of vehicles, enabling viewing a trend of one or more inconsistencies in the group of locations.

11. The vehicle inspection system of claim 1, wherein the controller displays a group of metrics for the group of items.

12. The vehicle inspection system of claim 1, wherein the controller facilitates communication with a group of remote experts.

13. The vehicle inspection system of claim 1, wherein the mobile inspection device is selected from a group consisting of a mobile phone, a head mounted display, mixed reality smart glasses, and a tablet computer.

14. The vehicle inspection system of claim 1, wherein the user input is generated using at least one of a gesture recognition system, wired gloves, a stereo camera, a gesture based controller, a mouse, a track ball, a keyboard, a track pad, a touch screen tablet, a motion sensing input device, a cyber glove, a camera, or a microphone.

15. The vehicle inspection system of claim 1, wherein the note is generated during one of a final inspection prior to delivery to a customer, maintenance, an assembly of the vehicle, and a certification of the vehicle.

16. An aircraft inspection system comprising:
a mobile inspection device;
a user interface for the mobile inspection device; and
a controller configured to operate with the mobile inspection device, wherein the controller is configured to identify a position of the mobile inspection device within an aircraft; receive a user input comprising a group of gestures made by a human operator with respect to an item in a field of view of the mobile inspection device based on the position of the mobile inspection device within the aircraft; create a note in association with the item in a group of items in the field of view of the mobile inspection device; and display the note in association with the item in the field of view on a display system for the mobile inspection device, enabling immersion in an augmented reality environment.

17. The aircraft inspection system of claim 16 further comprising:
a storage system in which a history of notes is stored.

18. The aircraft inspection system of claim 16, wherein the controller is configured to identify a set of notes in the field of view of the mobile inspection device for a current position of the mobile inspection device based on a policy applied to a role of the human operator of the mobile inspection device and display the set of notes on a graphical user interface on the display system.

19. The aircraft inspection system of claim 16, wherein the note comprises a graphical indicator and at least one of text, voice, an image, or a video.

20. The aircraft inspection system of claim 16, wherein the controller facilitates communication with a group of remote experts.

21. The aircraft inspection system of claim 16, wherein the note is generated during one of a final inspection prior to delivery to a customer, maintenance, an assembly of a vehicle, and a certification of the vehicle.

22. A method for inspecting a vehicle, the method comprising:
identifying a position of a mobile inspection device within the vehicle;
receiving a user input comprising a group of gestures made by a human operator with respect to an item in a group of items in a field of view of the mobile inspection device based on the position of the mobile inspection device;
creating a note at a location with respect to the vehicle in association with the item in the group of items in the field of view of the mobile inspection device in which the note is assigned to the location; and
displaying the note in association with the item in the field of view on a graphical user interface on a display system for the mobile inspection device.

23. The method of claim 22 further comprising:
storing the note in a storage system in which a history of notes is stored.

24. The method of claim 22 further comprising:
identifying a set of notes in the field of view of the mobile inspection device for a current position of the mobile inspection device; and
displaying the set of notes on the graphical user interface on the display system.

25. The method of claim 22, wherein a set of notes identified is based on a policy applied to a role of the human operator of the mobile inspection device.

26. The method of claim 22, wherein the displaying of the note in association with the item on the graphical user interface on the display system for the mobile inspection device forms at least one of a mixed reality environment or an augmented reality environment.

27. The method of claim 22, wherein the note comprises a graphical indicator and at least one of text, voice, an image, or a video; and the graphical indicator indicates a status selected from a group consisting of new, in progress, and completed.

* * * * *